US010322184B2

(12) United States Patent
Orizondo et al.

(10) Patent No.: US 10,322,184 B2

(45) Date of Patent: Jun. 18, 2019

(54) EMULSIONS FOR INTRAPULMONARY DELIVERY

(71) Applicants: Carnegie Mellon University, Pittsburgh, PA (US); The Regents of the University of Michigan, Ann Arbor, MI (US)

(72) Inventors: Ryan A. Orizondo, Pittsburgh, PA (US); Mario L. Fabiilli, Plymouth, MI (US); Keith E. Cook, Pittsburgh, PA (US)

(73) Assignees: Carnegie Mellon University, Pittsburgh, PA (US); The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 15/605,028

(22) Filed: May 25, 2017

(65) Prior Publication Data

US 2017/0340741 A1 Nov. 30, 2017

Related U.S. Application Data

(60) Provisional application No. 62/392,266, filed on May 25, 2016.

(51) Int. Cl.

| | |
|---|---|
| *A61K 47/34* | (2017.01) |
| *A61K 9/00* | (2006.01) |
| *A61K 47/24* | (2006.01) |
| *A61K 31/7036* | (2006.01) |
| *A61K 9/107* | (2006.01) |
| *A61K 9/12* | (2006.01) |
| *A61K 47/06* | (2006.01) |
| *A61K 47/22* | (2006.01) |

(52) U.S. Cl.

CPC .............. *A61K 47/34* (2013.01); *A61K 9/008* (2013.01); *A61K 9/0073* (2013.01); *A61K 9/107* (2013.01); *A61K 9/12* (2013.01); *A61K 31/7036* (2013.01); *A61K 47/06* (2013.01); *A61K 47/22* (2013.01); *A61K 47/24* (2013.01)

(58) Field of Classification Search

CPC ........ A61K 9/008; A61K 9/107; A61K 41/34; A61K 41/24; A61K 31/7036

See application file for complete search history.

(56) References Cited

U.S. PATENT DOCUMENTS

2012/0076777 A1* 3/2012 McLeay ............... A61K 9/0048 424/133.1

2013/0330389 A1* 12/2013 Fabiilli .............. A61K 41/0028 424/423

OTHER PUBLICATIONS

Holtze et al., Lab Chip, 2008, 8, p. 1632-1639. (Year: 2008).*

"Antibiotic Treatment for cystic fibrosis"; Third Edition; Cystic Fibrosis Trust; 2009.

Ciofu et al.; "Respiratory bacterial infections in cystic fibrosis"; Curr Opin Pulm Med; 2013; pp. 251-258; vol. 19.

Dolovich; "New Propellant-Free Technologies under Investigation"; Journal of Aerosol Medicine; 1999; pp. S-9-S-17; vol. 12.

Donaldson et al.; "Update on pathogenesis of cystic fibrosis lung disease"; Curr Opin Pulm Med; 2003; pp. 486-491; vol. 9.

Engel et al.; "Bioassays for Quantitating Ciprofloxacin and Tobramycin in Aqueous Humor"; Journal of Ocular Pharmacology; 1993; pp. 311-320; vol. 9:4.

Fabiilli et al.; "Delivery of Water-Soluble Drugs Using Acoustically-Triggered, Perfluorocarbon Double Emulsions"; Pharm Res.; 2010; pp. 2753-2765; vol. 27:12.

Flume et al.; "The Rationale for Aerosolized Antibiotics"; Pharmacotherapy; 2002; pp. 71S-79S; vol. 22.

Geller; "Aerosol Antibiotics in Cystic Fibrosis"; Respir Care; 2009; pp. 658-669; vol. 54:5.

Hino et al.; "Basic study for stabilization of w/o/w emulsion and its application to transcatheter arterial embolization therapy"; Advanced Drug Delivery Reviews; 2000; pp. 27-45; vol. 45.

Hirschl et al.; "Liquid ventilation provides uniform distribution of perfluorocarbon in the setting of respiratory failure"; Surgery; 1994; pp. 159-168; vol. 116.

Labiris et al.; "Pulmonary drug delivery. Part I: Physiological factors affecting therapeutic effectiveness of aerosolized medications"; Br J Clin Pharmacol; 2003; pp. 588-599; vol. 56.

Lam et al.; "Pharmacokinetic modelling of a once-daily dosing regimen for intravenous tobramycin in paediatric cystic fibrosis patients"; Journal of Antimicrobial Chemotherapy; 2007; pp. 1135-1140; vol. 59.

Lu et al.; Nebulized and intravenous colistin in experimental pneumonia caused by Pseudomonas aeruginosa; Intensive Care Med; 2010; pp. 1147-1155; vol. 36.

Miller et al.; "Aerosol Delivery and Modern Mechanical Ventilation"; Am J Respir Crit Care Med; 2003; pp. 1205-1209; vol. 168.

Mukhopadhyay et al.; "The quantitative distribution of nebulized antibiotic in the lung in cystic fibrosis"; Respiratory Medicine; 1994; pp. 203-211; vol. 88.

Novartis Pharmaceuticals Corporation; TOBI; Tobramycin Inhalation Solution: Prescribing Information; 2014.

Omri et al.; "Pulmonary Retention of Free and Liposome-Encapsulated Tobramycin after Intratracheal Administration in Uninfected Rats and Rats Infected with Pseudomonas aeruginosa"; Antimicrobial Agents and Chemotherapy; 1994; pp. 1090-1095; vol. 38:5.

Orizondo; "Antibacterial Perfluorocarbon Ventilation: A Novel Treatment Method for Bacterial Respiratory Infections"; Doctoral Dissertation; 2015; pp. 1-157; Retrieved from http://hdl.handle.net/2027.42/116728.

Orizondo et al.; "Characterization of a Reverse-Phase Perfluorocarbon Emulsion for the Pulmonary Delivery of Tobramycin"; Journal of Aerosol Medicine and Pulmonary Drug Delivery; 2014; pp. 392-399; vol. 27:5.

(Continued)

*Primary Examiner* — Jonathan S Lau

(74) *Attorney, Agent, or Firm* — The Webb Law Firm

(57) ABSTRACT

A therapeutic emulsion is provided comprising a perfluorocarbon emulsion and a therapeutic agent, such as tobramycin. Methods of making and using the emulsion are provided. A method of treating a lung infection is provided.

19 Claims, 4 Drawing Sheets

(56) References Cited

OTHER PUBLICATIONS

Orizondo et al.; "Effects of Emulsion Composition on Pulmonary Tobramycin Delivery During Antibacterial Perfluorocarbon Ventilation"; Journal of Aerosol Medicine and Pulmonary Drug Delivery; 2016; pp. 251-259; vol. 29:3.
Palmer et al.; "Aerosolized antibiotics in mechanically ventilated patients: Delivery and response"; Critical Care Medicine; 1998; pp. 31-39; vol. 26:1.
Papi et al.; "Infections and Airway Inflammation in Chronic Obstructive Pulmonary Disease Severe Exacerbations"; Am J Respir Crit Care Med; 2006; pp. 1114-1121; vol. 173.
Pennington; "Penetration of Antibiotics into Respiratory Secretions"; Reviews of Infectious Diseases; 1981; pp. 67-73; vol. 3:1.
Prayle et al.; "Aminoglycoside use in cystic fibrosis: therapeutic strategies and toxicity"; Current Opinion in Pulmonary Medicine; 2010; pp. 604-610; vol. 16.
Puchelle et al.; "Physical and Functional Properties of Airway Secretions in Cystic Fibrosis—Therapeutic Approaches"; Respiration; 1995; pp. 2-12; vol. 62.
Sethi et al.; "Infection in the Pathogenesis and Course of Chronic Obstructive Pulmonary Disease"; N Engl J Med; 2008; pp. 2355-2365; vol. 359.
Zhao; "Multiphase flow microfluidics for the production of single or multiple emulsions for drug delivery"; Advanced Drug Delivery Reviews; 2013; pp. 1420-1446; vol. 65.

* cited by examiner

FC-77

$C_8F_{18}$

+

$C_8F_{16}O$

Perflubron

$C_8BrF_{17}$

EMULSIONS FOR INTRAPULMONARY DELIVERY

CROSS REFERENCE TO RELATED APPLICATIONS

This application claims the benefit of U.S. Provisional Patent Application No. 62/392,266, filed May 25, 2016, which is incorporated herein by reference in its entirety.

STATEMENT REGARDING FEDERAL FUNDING

This invention was made with government support under Grant No. R03A1096029 awarded by the National Institutes of Health. The government has certain rights in the invention.

FIELD OF THE INVENTION

Provided herein are compositions useful for intrapulmonary drug delivery and related methods.

DESCRIPTION OF THE RELATED ART

Chronic bacterial respiratory infections are the primary cause of morbidity and mortality in patients with cystic fibrosis (CF) as well as the main cause of exacerbation in chronic obstructive pulmonary disease (COPD). Conditions such as CF and COPD feature changes in mucus rheology and mucociliary clearance that can make bacterial elimination exceedingly difficult.

In many cases, mucus thickening, impaired mucociliary clearance, a prolonged inflammatory state, and biofilm formation make treatment of lung infection exceedingly difficult. Systemic delivery of antibiotics results in limited diffusion of antibiotics from the epithelial lining fluid into the biofilm. This limits the effectiveness, requiring large dosages and increased systemic toxicity. Inhaled aerosolized antibiotics have shown the ability to achieve higher intrapulmonary antibiotic concentrations while limiting systemic toxicity and, as a result, have established an important role in treatment. However, there are still many shortcomings that make aerosolized delivery less than ideal. High mucus production by the infected host leads to poor ventilation in lung regions with the largest infectious burden, leading to ineffective delivery to these areas. In addition, a large percentage of the inhaled antibiotic is deposited in the mouth, throat, and upper airways, resulting in poor antibiotic penetration to the lower airways. The non-uniform intrapulmonary distribution of delivered antibiotics resulting from these challenges can hamper infection clearance as well as promote the development of antibiotic resistance. Improved treatments are needed for chronic and recurrent respiratory bacterial infections.

Antibacterial perfluorocarbon ventilation (APV) is a possible means of pulmonary antibiotic delivery in which the lungs are filled with aqueous antibiotics emulsified in perfluorocarbon (PFC) (i.e., water-in-PFC). During APV, the lungs are either partially filled with emulsion and ventilated with gas (partial APV) or fully filled and ventilated with emulsion (total APV). APV is proposed as a short-term 2 hours), adjunct therapy to systemic or inhaled antibiotics that could wash infected mucus from the lungs while delivering antibiotic to poorly ventilated regions.

The water-in-PFC emulsions used during APV consist of small droplets of aqueous antibiotic (e.g., 1-4 μm) suspended within a continuous PFC phase. Due to the immiscibility of water and PFC, a small amount of fluorosurfactant is used to stabilize the droplets and delay their coalescence by lowering the aqueous-PFC interfacial tension.

The potential advantage of APV is that it delivers antibiotic directly to the lungs where it is needed. The result is larger pulmonary antibiotic concentrations and lower systemic concentrations, which should lower the incidence of nephron- and oto-toxicity, e.g., for tobramycin. APV should also result in more spatially uniform delivery of drug throughout the lung relative to aerosolized pulmonary delivery because the effectiveness of aerosolized delivery is limited by its inherent dependence on airflow within the lung. Poor ventilation during disease due to lung damage or mucus plugging can result in significantly decreased aerosolized delivery to the most burdened regions of the lung. Furthermore, the significant effects of aerosolized particle size on site of deposition typically results in 25-90% of delivered drug being deposited in the oropharynx or delivery device, and thus never reaching the lung. Delivery is further impaired for patients on a mechanical ventilator in which approximately 20% or less of the delivered drug reaches the lung with the majority deposited in the delivery device and ventilator tubing. PFC, on the other hand, has shown uniform spatial distribution in the injured lung during liquid ventilation. Additionally, the physical characteristics that determine this distribution (viscosity and surface tension) are retained, and possibly enhanced, following the emulsification process. Thus, APV possesses the advantage of delivery of antibiotic directly to the lung with more spatially uniform drug distribution than inhaled antibiotics. It is therefore desirable to have compositions and methods for APV delivery that deliver adequate amounts of drug, e.g. antibiotic, to a patient in an acceptable temporal pattern.

SUMMARY

Provided herein is an emulsion including a perfluorocarbon continuous phase, an aqueous dispersed phase including a therapeutic agent, and a block copolymer fluorosurfactant composition in an amount ranging from an amount effective to produce a stable emulsion of the aqueous phase in the perfluorocarbon and an amount above which the emulsion cannot deliver a therapeutically-effective amount of the therapeutic agent to a patient, wherein the block copolymer fluorosurfactant has a hydrophilic block and a perfluorocarbon block.

Also provided herein is a method of delivering a therapeutic agent to lungs of a patient, including the step of administering to the patient an emulsion including a perfluorocarbon continuous phase, an aqueous dispersed phase including a therapeutic agent, and a block copolymer fluorosurfactant composition in an amount ranging from an amount effective to produce a stable emulsion of the aqueous phase in the perfluorocarbon and an amount above which the emulsion cannot deliver a therapeutically-effective amount of the therapeutic agent to a patient, wherein the block copolymer fluorosurfactant has a hydrophilic block and a perfluorocarbon block.

Further included herein is a method of making emulsion including the step of emulsifying a perfluorocarbon, an aqueous solution including a therapeutic agent, and a block copolymer fluorosurfactant composition having a hydrophilic block and a perfluorocarbon block in an amount ranging from an amount effective to produce a stable emulsion of the aqueous phase in the perfluorocarbon and an amount above which the emulsion cannot deliver a therapeutically-effective amount of the therapeutic agent to a patient.

DETAILED DESCRIPTION

Figure 1:
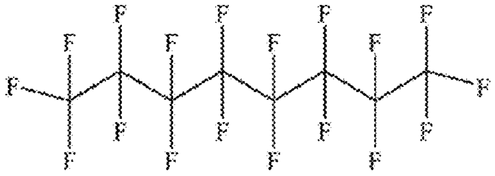
FIG. 1: Molecular structures of FC-77 and Perflubron.
Figure 1:
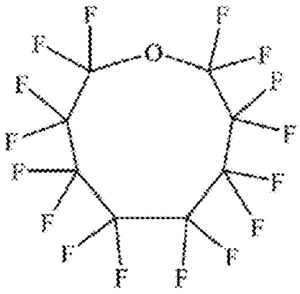
Figure 1:
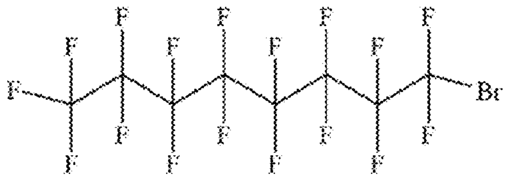

Other than in the operating examples, or where otherwise indicated, all numbers expressing quantities of ingredients, reaction conditions, and so forth used in the specification and claims are to be understood as being modified in all instances by the term "about". Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. Any numerical values, however, inherently contain certain errors necessarily resulting from the standard deviation found in their respective testing measurements. Furthermore, when numerical ranges of varying scope are set forth herein, it is contemplated that any combination of these values inclusive of the recited values may be used.

Also, it should be understood that any numerical range recited herein is intended to include all sub-ranges subsumed therein. For example, a range of "1 to 10" is intended to include all sub-ranges between and including the recited minimum value of 1 and the recited maximum value of 10, that is, having a minimum value equal to or greater than 1 and a maximum value of equal to or less than 10.

As used herein "a" and "an" refer to one or more.

As used herein, the term "comprising" is open-ended and may be synonymous with "including", "containing", or "characterized by".

As used herein, the term "polymer composition" is a composition comprising one or more polymers. As a class, "polymers" includes, without limitation, homopolymers, heteropolymers, co-polymers, block polymers, block co-polymers and can be both natural and synthetic. Homopolymers contain one type of building block, or monomer, whereas co-polymers contain more than one type of monomer.

A polymer "comprises" or is "derived from" a stated monomer if that monomer is incorporated into the polymer. Thus, the incorporated monomer that the polymer comprises is not the same as the monomer prior to incorporation into the polymer, in that at the very least, during incorporation of the monomer, certain groups, e.g. terminal groups, that are modified during polymerization are changed, removed, and/or relocated, and certain bonds may be added, removed, and/or modified. An incorporated monomer is referred to as a "residue" of that monomer. A polymer is said to comprise a specific type of linkage if that linkage is present in the polymer. Unless indicated otherwise, Mw refers to the weight average molecular weight of a polymer composition, or where otherwise applicable where simple molecular mass calculated from the atomic weights of the constituent atoms of a molecule. A "moiety" is a portion of a compound, and includes a residue or group of residues within a larger polymer.

By "biocompatible", it is meant that a device, scaffold composition, etc., and degradation products thereof, is essentially, practically (for its intended use) and/or substantially non-toxic, non-injurious or non-inhibiting or non-inhibitory to cells, tissues, organs, and/or organ systems that would come into contact with the device, scaffold, composition, etc. In the context of the compositions described herein, the compositions and their constituents are biocompatible, non-toxic, and/or pharmaceutically-acceptable in that they are safe for use in humans and/or animals—meaning that they are non-toxic, or substantially non-toxic within acceptable tolerances within the medical, pharmaceutical, and/or veterinary fields, such as according to requirements of governmental regulatory agencies for medical, pharmaceutical, and/or veterinary uses, such as the United States Food and Drug Administration.

A "drug substance", "therapeutic agent" or "active agent" means an active ingredient that is intended to furnish pharmacological activity or other direct effect in the diagnosis, cure, mitigation, treatment, or prevention of disease or to affect the structure or any function of the human body or animal. A "drug product" is a finished dosage form, for example, tablet, capsule, or solution that contains a drug substance, generally, but not necessarily, in association with one or more other ingredients. A drug product may be a composition of matter, object, or device, such as a liquid, solid, powder, capsule, tablet, ointment, cream, injectable, aerosol, patch, or any other physical form that is used to deliver an active agent, and can include single or multiple doses. Thus, in the example of a tobramycin-containing perfluorocarbon emulsion, the drug substance or active agent is tobramycin, while the drug product is the emulsion, or a single-use dispenser containing the ingredients for preparation of an emulsion comprising the tobramycin, a perfluorocarbon, and a fluorosurfactant. A "dosage form" refers to the form in which the drug product is marketed for use, e.g. as a capsule, sealed ampule, tablet, inhaler, nebulizer, drops, etc., and in one aspect of the invention, an emulsion, though the drug product may be provided in two phases to be sonicated immediately prior to use—that is, in sufficient time prior to administration such that the ingredients and emulsion remain stable until delivery to a patient.

The antibiotic tobramycin is often delivered to CF patients for treatment of chronic infections. A limitation of tobramycin treatment is that to avoid toxicity, the drug only can be delivered intermittently, for example once daily, with a sufficient period of time in which the blood levels of the drug are low enough to prevent the toxicity. For example, the drug often is administered in high doses once daily, leaving a sufficient period of time where systemic concentrations of the drug are low enough to prevent toxicity. To date, APV compositions have not been successful, resulting in delayed delivery of drug to animals, where optimal maximum systemic levels of the drug are never reached, and the drug persists at lower, but not safe levels in the blood of the animals, resulting in the possibility of toxicity.

It is believed, without any intent of being bound by this theory, that the use of excessive concentration of fluorosurfactant results in an emulsion that limits release and/or causes blockage of the active agent from contacting lung tissue and bacteria biofilm, resulting in delayed release of the active agent, thus preventing desirable bolus delivery of the active agent to the lung tissue and bacteria biofilm, and resulting in persistent lower, but toxic levels of the drug.

Optimization of APV requires an understanding of the temporal patterns of drug delivery and removal from the lung. However, the pharmacokinetics of these emulsions are more complicated than inhaled antibiotics. The pharmacokinetics during APV are a function of the aqueous volume percentage ($V_{aq}$), the aqueous antibiotic concentration ($C_{aq}$), and the fluorosurfactant concentration ($C_{fs}$). The $V_{aq}$ and $C_{aq}$ are defined as the percentage of aqueous phase in the emulsion and the antibiotic concentration within that aqueous phase, respectively. Together they define the total amount of drug delivered to the lungs upon initiating APV. The fluorosurfactant is responsible for maintaining emulsion stability and avoiding droplet coalescence and creaming. $C_{fs}$, therefore, affects the transport of antibiotic to the lung parenchyma and pulmonary capillaries. Throughout the work of the present invention, $C_{fs}$ values are specified as a ratio of fluorosurfactant mass to aqueous volume (i.e., mg per mL $H_2O$). As used herein, aqueous is water, or a liquid containing water as a solvent.

In optimizing the amounts of fluorosurfactant, a minimum amount is an amount that is required to form an emulsion and maintain a stable emulsion over the course of delivery to the lungs. According to one aspect of the invention, a maximum amount is less than an amount above which delivery of an effective amount of the therapeutic agent is not delivered to a patient, e.g., to lung tissue of a patient. In one example, the effective amount is determined by an agar release assay, e.g., in an assay as described herein in reference to FIG. 4. For example, in reference to FIG. 4, for FSH-PEG, the maximum value yielding 50% of the maximum effective concentration is ~11 mg/mL $H_2O$, yielding an exemplary effective range of from 0.5 to 11 mg/mL $H_2O$, with the optimum (maximum delivery rate) falling between 0.5 mg/mL $H_2O$ to 2 mg/mL $H_2O$ of range. In another example in reference to FIG. 4, for the combination of FSL-PEG and FSL oil as the fluorosurfactant, the maximum is approximately 10 mg/mL $H_2O$. In a further aspect, the amount of fluorosurfactant is less than 11 mg/mL of water in the emulsion, e.g., from >0 to 10 mg/mL of water in the emulsion.

"Perfluorocarbons are clear, odorless liquids composed primarily of covalently bonded carbon and fluorine atoms, having, for example and without limitation, the formula $C_xF_y$, including ethers thereof. A perfluorocarbon having one or more ether linkages is termed a "perfluoroether", and can be cyclic (perfluorocycloether). Perfluorocarbons include single compounds and mixtures of compounds, such as the mixture of perfluorocycloether and perfluorooctane described below. Perfluorocarbons are broadly-known and many are commercially available, including those that have been studied for medical or pharmacological purposes, including breathing, respiratory therapies, imaging, and drug delivery. Perfluorocarbons as a class include substituted perfluorocarbons in which one or more heteroatoms are added, such as, for example and without limitation, O in the case of ethers, and Br in the case of Perflubron (perfluorooctylbromide). Perfluorocarbons may be linear, branched, cyclic, or combinations thereof and are saturated, and in various aspects include from six to twelve carbon atoms. Although there are many different types of PFCs suitable for LV, virtually all clinical LV trials have utilized Perflubron (perfluorooctyl bromide). Much of the LV work done in animals has also utilized FC-77 (mixture of perfluorocycloether and perfluorooctane). The molecular structures of both Perflubron and FC-77 are shown in FIG. 1. According to one aspect of the invention, the perfluorocarbons described herein, as well as other compositions useful in forming the drug-delivery emulsion composition described herein, such as the fluorosurfactant, and the constituents of the aqueous phase, are biocompatible, non-toxic, and/or pharmaceutically-acceptable.

Due primarily to the extremely strong covalent bonding between carbon and fluorine atoms (C—F bonds are 485 kJ/mol), PFCs have high intramolecular forces and tend to be very stable. In a biological environment, this translates to PFCs being bioinert and resisting any type of metabolism or enzymatic changes. PFCs are also nonpolar and tend to have very low intermolecular, or van der Waals, forces. These low intermolecular forces are responsible for many of the properties of PFC critical to LV. First, due to these weak forces, PFCs tend to be quite volatile, with those used during LV typically evaporating at or below physiological temperatures. Second, weak van der Waals forces also give PFCs a very low surface tension (<20 dyne/cm) which allow them to effectively penetrate the minute spaces of the small airways and alveoli. Lastly, and perhaps most importantly, it is these weak intermolecular forces that make PFC an excellent solvent for gases such as oxygen and carbon dioxide (solubility of ~50 mL $O_2$ and 140-210 mL $CO_2$ per dL of PFC). PFCs are also fairly dense (about twice that of water) and not soluble with water or lipids. As such, PFCs are immiscible with virtually all physiological substances other than gases.

The concept of using liquid PFC to support respiration was first demonstrated in mice nearly 50 years ago. Over time, LV techniques were refined and systems which mechanically assisted the movement of liquid tidal volumes to and from the lungs were developed. In its more recent use, two modes of LV were developed: partial liquid ventilation (PLV) and total liquid ventilation (TLV). During PLV, the lungs are partially filled with liquid PFC (typically to end-expiratory volume) and gas ventilated with a conventional ventilator. In this setting, gas exchange occurs within the liquid PFC during each breath as oxygen-rich air is mixed with PFC within the larger airways. During TLV, the lungs are completely filled with liquid PFC and tidal volumes of PFC are moved into and out of the lungs typically using a piston pump. Additionally, a parallel, extracorporeal circuit continually achieves gas exchange within the PFC (oxygenation and $CO_2$ removal) while also filtering and heating the liquid. Due to the need for specialized equipment during TLV, PLV is considered much easier to implement in to clinical practice. Following LV, PFC can be mostly suctioned from the lung or left to evaporate. The majority of PFC left in the lung evaporates, is exhaled, and cleared from the lung within seven days of instillation. The rate of evaporative PFC clearance from the lung has been shown to be largest immediately following administration and steadily declines thereafter. Additionally, clearance tends to occur in the nondependent regions of the lung first. Although small amounts of PFC may be transported across the lung epithelium into the systemic circulation, this amount has been shown to be less than 1% of the administered dose. Virtually all delivered PFC is believed to ultimately leave the body via evaporation through the lung or transpiration through the skin. Even PFC delivered to the systemic circulation in the form of an emulsion for use as an imaging agent or blood substitute has been shown to be cleared via expired air after phagocytosis by reticuloendothelial macrophages. Although trace amounts of PFC have been shown to preferentially accumulate in fatty tissues and remain for relatively long periods of time, there has been no evidence of any negative consequences. Along the same lines, the long-term effects and toxicity of PFC have been studied extensively in animals and patients for periods up to 10 years without evidence of adverse effects. Further description of perfluorocarbons and their benefits are described in Orizondo, R. A. (2015) *Antibacterial Perfluorocarbon Ventilation: A Novel Treatment Method for Bacterial Respiratory Infections* (Doctoral dissertation). Retrieved from http://hdl.handle.net/2027.42/116728.

Additionally, the fluorosurfactant stabilizes the aqueous drug phase within the PFC phase. If $C_{fs}$ is too small, the dispersion of drug is not maintained following sonication. The aqueous droplets quickly rises out of the PFC phase, and the ability of the emulsion to generate improved pulmonary distribution of the drug is lost. However, if the $C_{fs}$ is too great, the aqueous phase of the emulsion is inhibited from coalescing with surrounding aqueous media, including mucus and biofilm lining the lung tissue. This inhibits delivery of the drug to the bacteria and lungs (FIGS. 3A-3C and 4).

Figure 2:
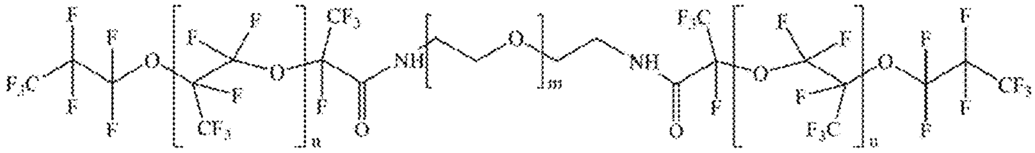
FIG. 2. Molecular structure of a copolymer of Krytox 157 FS and PEG.

A "fluorosurfactant" is a compound that facilitates production of a stable emulsion of a perfluorocarbon and an aqueous phase, such as water, saline (e.g. normal saline), phosphate-buffered saline (PBS), a salt solution, optionally comprising a water-soluble therapeutic agent or therapeutic composition, such as a micro- or nano-particle, or a drug-carrier complex, for example and without limitation, a drug-cyclodextrin composition in which an active agent is complexed with a cyclodextrin or a cyclodextrin derivative. According to one aspect, a fluorosurfactant compound includes a fluorophilic segment, such as a perfluorocarbon segment, block, or moiety, that partitions to a perfluorocarbon, and a hydrophilic segment, block, or moiety, such as a linear or branched block copolymer of a perfluorocarbon and a poly($C_2$-$C_4$ alkyl)ether, such as a polyoxyethylene, polyoxyproplyene, or polyoxybutylene. Copolymer block size, polydispersity, and overall Mw of the block copolymer can be optimized for any emulsion composition. As described herein and in Fabiilli M L, et al. (Delivery of water-soluble drugs using acoustically triggered perfluorocarbon double emulsions. *Pharm Res.* 2010; 27:2753-2765), a suitable fluorosurfactant is a block copolymer comprising a perfluorocarbon (perfluoroether) segment and a polyoxyethylene (polyethyleneglycol or PEG) segment, for example and without limitation the triblock copolymer condensation product of a carboxylated perfluoroether with a PEG diamine, such as the Krytox 157 FSL and PEG block copolymer composition of Fabilli M L et al. An example of a Krytox-PEG block copolymer is shown in FIG. 2. In one example, described below, the copolymer uses a low molecular weight version of Krytox 157FS (FSL), where n=13 (Mw=2,500 Da) and a larger PEG segment where m=75 (Mw=3,350 Da), resulting in a block copolymer composition having a Mw of 8,350 Da. In another example, described below, the copolymer uses a high molecular weight version of Krytox 157FS (FSH), where n=41 (Mw=7.000-7,500 Da) and a smaller PEG segment where m=22 (Mw=1,000 Da), resulting in a block copolymer composition having a Mw of 15,500 Da. In one aspect, the fluorosurfactant is a block copolymer, e.g. a triblock copolymer, having a Mw in the range of from 500 Da to 20000 Da. The hydrophilic segment, e.g. poly(oxyalkylene) or PEG segment, of the block copolymer or triblock copolymer has a Mw ranging from 100 Da to 5000 Da. The perfluorocarbon segment, e.g. perfluoroether segment, of the block copolymer or triblock copolymer has a Mw ranging from 300 Da to 10000 Da. In one aspect, in reference to the Krytox-PEG composition depicted in FIG. 2, m ranges from 22 to 75, and n ranges from 13 to 41.

An "emulsion" is a stable mixture of two or more immiscible liquids held in suspension by an emulsifier. The emulsion comprises a continuous phase and a dispersed phase dispersed, e.g., as droplets, within the continuous phase. In the context of the present invention, the two immiscible liquids are the perfluorocarbon and the aqueous phase e.g. comprising the active agent in any suitable form, and the emulsifier is the fluorosurfactant. The perfluorocarbon forms the continuous phase and the aqueous phase is dispersed within the perfluorocarbon. Emulsions can be formed by a variety of processes as are known in the art, for example and without limitation by physical mixing, e.g. shaking, stirring, blending or homogenizing, or by sonication, e.g., by ultrasonication as described below. Pharmaceutically-acceptable emulsions are often produced by sonicating a two-phase composition prior to use, e.g. at the bedside or pharmacy, such as in a hospital pharmacy immediately prior to use. A "stable emulsion" in the context of the present invention is an emulsion that substantially remains in an emulsified state prior to delivery of the emulsion into the lungs of a patient, and therefore remains an emulsion at, for example, from 20° C. to 37° C. for a time period sufficiently long enough to deliver a therapeutically-effective amount of the emulsion to the lungs of a patient. As described below, in one example stability of an emulsion may be measured by obtaining a mid-level sample of an emulsified solution allowed to sit in a centrifuge tube without agitation at room temperature for five minutes after emulsification, and determining if a therapeutically-effective amount of the composition remains in that mid-level sample. If the solution does not resolve into two phases, and a therapeutically-effective amount of the therapeutic agent remains in the mid-level sample, then the emulsion is considered stable. As described in the Examples below, an agar diffusion test (zone of inhibition test), may be used to determine and optimize emulsion formulations to deliver therapeutically effective amounts of a therapeutic agent, such as tobramycin.

An effective amount of the fluorosurfactant composition in terms of the emulsions described herein may be a minimum amount of the fluorosurfactant composition able to produce a stable emulsion. In aspects, an effective amount of the fluorosurfactant is an amount within a range including at its lower end that minimum amount of the fluorosurfactant composition able to produce a stable emulsion and at its upper end an amount of the fluorosurfactant that retains the ability of the emulsion to deliver an effective amount of a therapeutic composition to lung tissue of a patient, for example as measured using an agar diffusion test. In one aspect, the fluorosurfactant is present in a minimal amount, including the minimum amount and amounts insignificantly greater than that minimum amount and that are amounts of fluorosurfactant that result in an emulsion that is capable of delivering a therapeutically-effective amount of a therapeutic agent.

In one aspect, the minimal amount ranges from a minimum amount of fluorosurfactant able to produce a stable emulsion to a maximum amount of fluorosurfactant above which the emulsion is impaired or unable to deliver therapeutically-effective amounts of the therapeutic agent, and is represented by the equation 20*log(1+Y), in which Y=the minimum concentration of fluorosurfactant able to produce a stable emulsion. For example, and without limitation, a range of suitable fluorosurfactant concentrations, where a minimum amount useful to produce a stable emulsion is 0.01 mg/mL, can be 0.01-0.086 (20*log(1+0.01)). In other aspects, a range of suitable fluorosurfactant concentrations can have minimum values of 0.1, 0.6, 2, 5, or 10 mg/mL or $H_2O$, and a corresponding maximum value of 0.83 (20*log (1+0.1), 4.1 (20*log(1+0.6)), 9.5 (20*log(1+2)), 15.6 (20*log(1+5)), or 20.8 (20*log(1+10)) mg/mL or $H_2O$, respectively. As used herein, "log(z)" refers to the base 10 logarithm of z ($\log_{10}(z)$), where z is any number, such as 1+Y as described above.

For example, the maximum amount of the fluorosurfactant is greater than 100% (e.g., in terms of mg of the fluorosurfactant composition per mL of water or aqueous solution) of that minimum amount (concentration) and providing an amount of the fluorosurfactant that retains the ability of the emulsion to deliver an effective amount of a therapeutic composition to lung tissue of a patient, for example as measured using an agar diffusion test, such as, for example and without limitation: 101%, 105%, 110%, 115%, 120%, 125%, 130%, 140%, 150%, 200%, or greater, of the minimum amount of the fluorosurfactant composition able to produce a stable emulsion, and increments therebetween. For example the upper end may be no more than 110% or 120% of the minimum amount of the fluorosurfactant composition able to produce a stable emulsion. As a non-limiting example, if a minimum amount of the fluorosurfactant composition able to produce a stable emulsion is 10 mg per mL of $H_2O$ in the emulsion, a maximum amount of the fluorosurfactant that is capable of producing an emulsion for delivering an effective amount of a given therapeutic agent to lungs of a patient, e.g., as measured in an agar diffusion test, may be 120% of the minimum amount, or 12 mg of the fluorosurfactant composition per mL of $H_2O$.

In another example, the maximum amount of the fluorosurfactant is no more than 1, 2, 3, 4, 5, 6, 7, 8, 9, or 10 mg/mL of water or aqueous phase in the emulsion greater than the minimum amount of fluorosurfactant able to produce a stable emulsion—for example, no more than one or two mg of fluorosurfactant per mL of the aqueous phase or water in the emulsion greater than that minimum amount. The aqueous phase is present in the emulsion in an amount effective for delivery of a therapeutic agent, and in one aspect ranges be 0.005% to 10% (v/v), and in another aspect ranges from 0.01% to 5% v/v, for example, from 0.1% to 2.5% v/v, or 0.2% v/v.

Based on the preceding, a person of ordinary skill in the art can readily determine empirically for any combination of perfluorocarbon, aqueous solution, therapeutic agent and fluorosurfactant composition, a minimum amount of the fluorosurfactant composition able to produce a stable emulsion, and therefore an amount of a fluorosurfactant, such as a minimal amount as described above, able to deliver a therapeutically effective amount of a therapeutic agent to lungs of a patient, e.g., as measured in an agar diffusion test.

An "antibiotic" is an antimicrobial drug used, for example, to treat infections. "Aminoglycoside antibiotics" are antibiotics comprising amino-modified sugar (glycoside) residues. Non-limiting examples of aminoglycoside antibiotics include: streptomycin, kanamycin, tobramycin, paromomycin, netilmicin, amikacin, gentamicin, and neomycin. Other antibiotics include: penicillins, cephalosporins, rifamycins, lipiarmycins, quinolones, sulfonamides, macrolides, lincosamides, tetracyclines, cyclic lipopeptides, glycylcyclines, oxazolidinones, and lipiarmycins. A non-limiting list of antibiotics includes, without limitation: acyclovir, ofloxacin, ampicillin, amphotericin B, atovaquone, azithromycin, ciprofloxacin, clarithromycin, clindamycin, clofazimine, dapsone, diclazuril, doxycycline, erythromycin, ethambutol, fluconazole, fluoroquinolones, foscarnet, ganciclovir, gentamicin, itraconazole, isoniazid, ketoconazole, levofloxacin, lincomycin, miconazole, neomycin, norfloxacin, ofloxacin, paromomycin, penicillin, pentamidine, polymyxin B, pyrazinamide, pyrimethamine, rifabutin, rifampin, sparfloxacin, streptomycin, sulfadiazine, tetracycline, tobramycin, trifluorouridine, trimethoprim sulfate, Zn-pyrithione, and silver salts such as chloride, bromide, iodide and periodate.

Additional active agents that may be incorporated into the emulsion include, without limitation, anti-inflammatories, such as, without limitation, NSAIDs (non-steroidal anti-inflammatory drugs) such as salicylic acid, indomethacin, sodium indomethacin trihydrate, salicylamide, naproxen, colchicine, fenoprofen, sulindac, diflunisal, diclofenac, indoprofen sodium salicylamide, anti-inflammatory cytokines, and anti-inflammatory proteins or steroidal anti-inflammatory agents); anticlotting factors such as heparin, Pebac, enoxaparin, aspirin, hirudin, plavix, bivalirudin, prasugrel, idraparinux, warfarin, coumadin, clopidogrel, PPACK, GGACK, tissue plasminogen activator, urokinase, and streptokinase; growth factors; immunosuppressants; glucocorticoids such as hydrocortisone, betamethasone, dexamethasone, flumethasone, isoflupredone, methylprednisolone, prednisone, prednisolone, and triamcinolone acetonide; anti-angiogenics such as fluorouracil, paclitaxel, doxorubicin, cisplatin, methotrexate, cyclophosphamide, etoposide, pegaptanib, lucentis, tryptophanyl-tRNA synthetase, retaane, CA4P, AdPEDF, VEGF-TRAP-EYE, AG-103958, Avastin, JSM6427, TG100801, ATG3, OT-551, endostatin, thalidomide, bevacizumab, neovastat; anti-proliferatives such as sirolimus, paclitaxel, perillyl alcohol, farnesyl transferase inhibitors, FPTIII, L744, anti-proliferative factor, Van 10/4, doxorubicin, 5-FU, Daunomycin, Mitomycin, dexamethasone, azathioprine, chlorambucil, cyclophosphamide, methotrexate, mofetil, vasoactive intestinal polypeptide, and PACAP; antibodies or fragments thereof; and nitric oxide donors or precursors, such as, without limitation, Angeli's Salt, L-Arginine, Free Base, nitrates, nitrites, Diethylamine NONOate, Diethylamine NONOate/AM, Glyco-SNAP-1, Glyco-SNAP-2, (.+-.)-S-Nitroso-N-acetylpenicillamine, S-Nitrosoglutathione, NOC-5, NOC-7, NOC-9, NOC-12, NOC-18, NOR-1, NOR-3, SIN-1, Hydrochloride, Sodium Nitroprusside, Dihydrate, Spermine NONOate, Streptozotocin. Further examples of additional active agents include: basic fibroblast growth factor (bFGF or FGF-2), acidic fibroblast growth factor (aFGF), nerve growth factor (NGF), vascular endothelial growth factor (VEGF), hepatocyte growth factor (HGF), transforming growth factor-beta pleiotrophin protein, midkine protein, platelet-derived growth factor (PDGF) and angiopoietin-1 (Ang-1). Additional classes of therapeutic agents include: genetic material, e.g., nucleic acids and nucleic acid analogs, e.g., intended for gene modification using CRISPR-Cas9, viral vectors, interfering RNA (RNAi), such as microRNA (miRNA), or small interfering RNA (siRNA), or other forms of delivery of genetic material, such as by viral transducing particles, nanoparticles; pulmonary surfactant replacement materials; cells, such as differentiated, progenitor or multipotent cells, including stem cells, autogenous, or allogeneic cells; delivery of peptides or protein, such as enzymes or insulin; and/or mucolytics, expectorants, or and mucokinetic drugs. In yet another aspect, the therapeutic agent is a dissolved metallic substance, such as silver of copper ions, having a therapeutic or antimicrobial effect.

Active agents are included in the delivery system described herein, and are administered in desired or specified amounts, and/or in amounts effective to achieve a desired end-point, such as reduction in inflammation, epithelial cell repair and growth, breakdown and clearance of proteinaceous and cellular debris, genetic engineering, cancer treatment, replacement of pulmonary surfactant, and mobilization and clearance of mucus. In various aspects, the emulsion is administered to a patient in an amount effective to achieve a therapeutic objective, e.g., to treat a lung infection, such as an infection associated with cystic fibrosis, pneumonia, chronic obstructive pulmonary disease, tuberculosis, or inhaled pathogens involved in biological warfare.

The emulsion composition is made by any useful emulsification method. In aspects, the emulsion is manufactured by mixing, blending, homogenizing, sonicating, or microfluidics (see, e.g., Xiao, C, Multiphase flow microfluidics for the production of single or multiple emulsions for drug delivery *Adv. Drug Deliv. Rev.* 2013; 65(11-12):1420-1446). Those of ordinary skill are able to produce emulsions according to these broadly-known methods.

The emulsion compositions described herein may be administered to a patient's lungs by any effective method. In one aspect, the emulsion is administered as a spray, for example as an aerosol employing any useful spray device or nebulizer, as are broadly-known in the pharmaceutical and medical arts. In one aspect, the composition comprises a pharmaceutically-acceptable aerosol propellant. In another aspect, the composition is delivered using a nebulizer device as are broadly known in the pharmaceutical and medical arts. In yet another aspect, the composition is delivered using a total or partial liquid ventilation method, as are broadly-known, for example and without limitation as described herein.

EXAMPLES

Preparation of Tobramycin Loaded Water-in-PFC Emulsion

Tobramycin-loaded, water-in-PFC emulsions were prepared as follows. In brief, a mixture of PFC, aqueous tobramycin, and fluorosurfactants was emulsified via sonication (Model S-450D, 20 kHZ, 3.2 mm diameter microtip; Branson Ultrasonics, Danbury, Conn., USA) at 200 $W/cm^2$ for 60 seconds. Emulsion was prepared in 10-mL batches.

The fluorosurfactants used in this work are perfluoroether-polyethelene glycol (PEG) triblock copolymers synthesized from Krytox 157FS oils (Dupont, Wilmington, Del., USA) as described in M. L. Fabiilli, et al. *Pharm Res,* 27 (2010) 2753-2765. Two different variations of the triblock copolymer were evaluated in the present study. A low molecular weight perfluoroether (Krytox 157FSL, Mw=2,500 Da, n=13) was used with a relatively large PEG block (Mw=3,350 Da, m=75) (see FIG. 2). This copolymer and its low molecular weight perfluoroether component will subsequently be referred to as FSL-PEG and FSL, respectively. The current study also explored the use of a modified version of the triblock copolymer, termed FSH-PEG. The FSH-PEG copolymer was synthesized in an identical manner to that for FSL-PEG but utilizes a larger perfluoroether (Krytox 157FSH, Mw=7,000-7,500 Da, n=41) with a smaller PEG block (molecular weight=1,000 Da, m=22). Ultimately, these modifications resulted in an increase in the fluorophilic portion of the molecule relative to the hydrophilic portion. This is most easily recognized by comparing a ratio of the Mw of the fluorophilic blocks to the hydrophilic block within each polymer. Such ratios are 1.5:1 and 14.5:1 for FSL-PEG and FSH-PEG, respectively. The intent of such modifications was to increase the fluorophilicity of the copolymer such that it could be used alone, rather than in combination with its perfluorocarbon form, lacking a hydrophilic (PEG) block.

The fluorosurfactant concentrations and molarities discussed in the remainder of this example take in to account the total amount fluorosurfactant used for any particular emulsion formulation. Thus, in the case of emulsion formulations using FSL-PEG and FSL, the concentrations or molarities discussed are based on the sum of the masses or moles of each molecule. The fluorosurfactant concentrations used for any particular emulsion formulation are specified as a ratio of fluorosurfactant mass to aqueous volume (i.e., mg per mL $H_2O$). Similar to previous work with APV, the PFC used in all experiments was perfluorocycloether/perfluorooctane (FC-770; 3M Inc., St. Paul, Minn., USA).

Evaluation of Drug Emulsification and Availability

The presence and availability of emulsified tobramycin was quantified via the commonly used agar well diffusion method of measuring antibiotic content. In this method, the surface of LB agar plates is inoculated with 500 μL of mid-log growth *Pseudomonas aeruginosa* in tryptic soy broth. Similar methods are disclosed in Omri et al. Pulmonary Retention of Free and Liposome-Encapsulated Tobramycin after Intratracheal Administration in Uninfected Rats and Rats Infected with *Pseudomonas aeruginosa*. Antimicrobial Agents and Chemotherapy. 1994, 38: 1090-1095. Briefly, during such a measurement, a liquid sample of unknown antibiotic concentration is dispensed into a cylindrical well within inoculated agar (using a bacterial strain susceptible to the antibiotic of interest), thereby creating a large surface area of contact between the liquid sample and a primarily aqueous surface (i.e., the agar gel). The agar plate is then incubated and the sample allowed to completely evaporate. During this stage, the antibiotic within the sample diffuses into the agar and creates a circular zone of inhibited bacterial growth with a radius proportional to the unknown antibiotic concentration. Initially, in order to isolate the effects of fluorosurfactant type and concentration, emulsions with fixed $V_{aq}$ (2.5%) and $C_{aq}$ (40 mg/mL) were examined with $C_{fs}$ values of 0.5-96 mg/mL $H_2O$ for each of the two fluorosurfactant types. Following this evaluation, the effects of $V_{aq}$ and $C_{aq}$ were assessed using emulsions with $C_{fs}$=2 mg/mL $H_2O$ of FSH-PEG, $V_{aq}$=0.5-2.5%, and $C_{aq}$=40-200 mg/mL. $V_{aq}$ and $C_{aq}$ were varied inversely to maintain a constant total tobramycin content of 1 mg/mL of emulsion. The specific emulsion formulations used are shown in Table 1.

TABLE 1

Emulsion formulations evaluated during assessment of tobramycin availability.

| Fluorosurfactant Type [—] | $C_{fs}$ [mg per mL $H_2O$] | $V_{aq}$ [%] | $C_{aq}$ [mg $mL^{-1}$] | Total Loaded Tobramycin Mass [mg per mL emulsion] |
|---|---|---|---|---|
| FSL-PEG + FSL | 0.5 | 2.5 | 40 | 1 |
| FSL-PEG + FSL | 2.0 | 2.5 | 40 | 1 |
| FSL-PEG + FSL | 4.0 | 2.5 | 40 | 1 |
| FSL-PEG + FSL | 10.0 | 2.5 | 40 | 1 |
| FSL-PEG + FSL | 30.0 | 2.5 | 40 | 1 |
| FSL-PEG + FSL | 96.0 | 2.5 | 40 | 1 |
| FSH-PEG | 0.5 | 2.5 | 40 | 1 |
| FSH-PEG | 2.0 | 2.5 | 40 | 1 |
| FSH-PEG | 4.0 | 2.5 | 40 | 1 |
| FSH-PEG | 10.0 | 2.5 | 40 | 1 |
| FSH-PEG | 30.0 | 2.5 | 40 | 1 |
| FSH-PEG | 96.0 | 2.5 | 40 | 1 |
| FSH-PEG | 2.0 | 0.5 | 200 | 1 |
| FSH-PEG | 2.0 | 1.0 | 100 | 1 |

For each formulation evaluated, approximately 10 mL of emulsion was prepared in a 15-mL centrifuge tube and allowed to sit at room temperature without agitation for five minutes before sampling. Three samples (75 μL/sample) of emulsion were taken from the middle height of the emulsion (i.e., midway between the conical bottom and emulsion surface) in order to capture the effects of creaming and phase separation within the emulsion. The stability of such emulsions have shown that drug content at the middle height of a column of emulsion at five minutes post-preparation is indicative of content throughout the bulk of the emulsion for up to four hours post-preparation. Emulsion samples were placed directly into wells within LB agar plates inoculated with *Pseudomonas aeruginosa* (PA) that were prepared as described in R. A. Orizondo, et al. Effects of Emulsion Composition on Pulmonary Tobramycin Delivery During Antibacterial Perfluorocarbon Ventilation, *J Aerosol Med Pulm Drug Deliv*, DOI 10.1089/jamp.2015.1235(2016). Aqueous samples of known tobramycin concentration were also loaded into identically prepared wells for later comparison. Plates were then incubated at 37° C. for 24 hours, thereby allowing the sample volume (either emulsion or aqueous tobramycin) within each well to completely evaporate. Following incubation, circular inhibition zones produced by tobramycin that had diffused into the agar were imaged and measured. Interpolation from the inhibition zones of aqueous standard solutions was then used to determine effective tobramycin concentrations (i.e., the aqueous tobramycin concentration resulting in an identical inhibition area) for each emulsion evaluated. An aqueous tobramycin solution with a concentration of 5 μg/mL produced the smallest measurable inhibition zone. Emulsion samples resulting in immeasurably small inhibition zones were assigned an equivalent aqueous tobramycin concentration of 2.5 μg/mL for further analysis. Each prepared emulsion was tested in triplicate and averaged to produce a single measurement for each trial. Three separate trials were performed for each emulsion formulation evaluated.

In order to further confirm the role of fluorosurfactant in drug availability, a modified exposure procedure from that described above was also performed. Aliquots of an emulsion with a formulation exhibiting the largest effective tobramycin concentration were sampled as described above. Prior to the addition of samples to the agar wells, the wells were first filled (75 μL/well) with a solution of FSH-PEG dissolved in PFC (2.4 mg/mL, containing no drug or aqueous phase) and allowed to rest at room temperature for 10 minutes. The concentration of FSH-PEG in PFC used for the pre-exposure is equivalent to an emulsion ($V_{aq}$=2.5%) with the maximum $C_{fs}$ value examined (96 mg/mL $H_2O$) with no aqueous phase present. Following the exposure, the FSH-PEG/PFC solution was thoroughly aspirated from each well and the emulsion samples added. Agar plates were then incubated and processed in an identical manner as that described above.

In order to distinguish between decreased drug diffusion due to impaired drug availability versus decreased drug presence caused by phase separation prior to sampling, the absolute tobramycin content within the emulsion was evaluated in conjunction with all availability trials described above. This evaluation used the identical agar well diffusion method described above but was preceded by a phase inversion and separation process to mechanically separate the drug-containing aqueous phase out of the emulsion. More specifically, two samples (240 μL/sample) of emulsion were taken in an identical manner as that described for the availability assessment (five minutes post-sonication from middle height). The samples were then diluted with 8 mL of sterile water and re-sonicated at 200 W/$cm^2$ for one minute, resulting in an inverted emulsion (continuous aqueous phase with dispersed PFC phase). The inverted emulsion was then centrifuged at 3,000 g for 20 minutes in order to separate the PFC and aqueous phases. Samples from the aqueous phase were loaded into wells (75 μL/well) within inoculated agar along with standard solutions of known tobramycin concentration and assayed as described above. Each sample was measured in triplicate and the resulting values averaged to produce a single concentration. The concentration for each of the two samples for a given emulsion were averaged to produce a single value for each trial and three separate trials performed for each emulsion formulation. Some samples resulted in a secondary zone of affected bacterial growth outside of the inner zone of completely inhibited growth. This effect occurred primarily from emulsion or aqueous samples with high tobramycin content. In such cases, measurement of the inner zone of completely inhibited growth was used for all analysis.

All emulsion formulations evaluated had a loaded drug mass of 1 mg tobramycin per mL emulsion. Assuming that the tobramycin was homogenously distributed throughout the emulsion and all tobramycin was recovered during the emulsion inversion process, the assayed aqueous phase would have a tobramycin concentration of 30 μg/mL. Experimental values from this study were normalized by this value and are thus reported as a percentage of the loaded drug mass. Samples from emulsions using either fluorosurfactant type at the largest $C_{fs}$ value (96 mg/mL $H_2O$) with sterile saline in the aqueous phase were also examined via the methods described for both drug emulsification and availability as negative controls.

Lastly, in order to quantify the availability of emulsified tobramycin, the measured effective concentration was normalized by the measured tobramycin content according to the following equation:

$$\text{normalized tobramycin availability}[\%] = \frac{\text{effective tobramycin concentration}\left[\frac{\mu g}{mL}\right]}{\text{tobramycin content}\left[\frac{\mu g}{mL}\right]}$$

Statistical Analysis

SPSS 22 (IBM Corporation, Armonk, N.Y., USA) was used to perform all statistical analysis. A one- or two-way ANOVA was used to determine significant effects for the tobramycin content and availability data. The Bonferroni method was applied to determine significance between comparisons of interest. An independent t-test was used to determine the effect of pre-exposing the agar well to FSH-PEG on tobramycin availability. All subsequent reported values are given as mean±standard deviation and all error bars in presented Figures represent standard deviations.

Results and Discussion

Figure 3A:
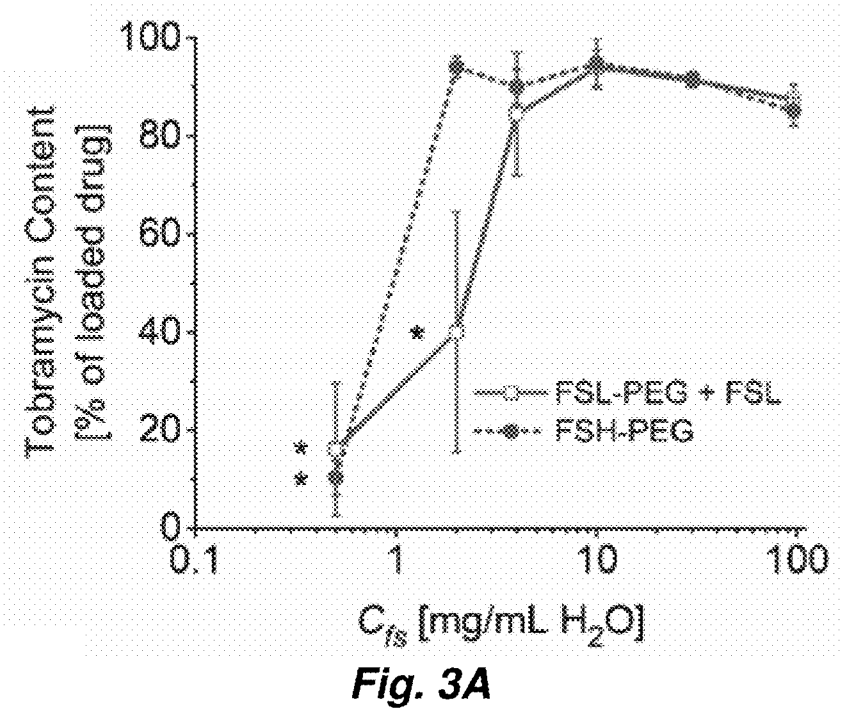
FIG. 3A-FIG. 3C: Tobramycin content (FIG. 3A), effective concentration (FIG. 3B), and normalized availability (FIG. 3C) as a function of $C_{fs}$ for emulsions utilizing $V_{aq}$=2.5%, $C_{aq}$=40 mg/mL, and FSL-PEG+FSL or FSH-PEG. n=3 for each condition and an asterisk denotes statistically significant ($p<0.01$) differences.
Figure 3B:
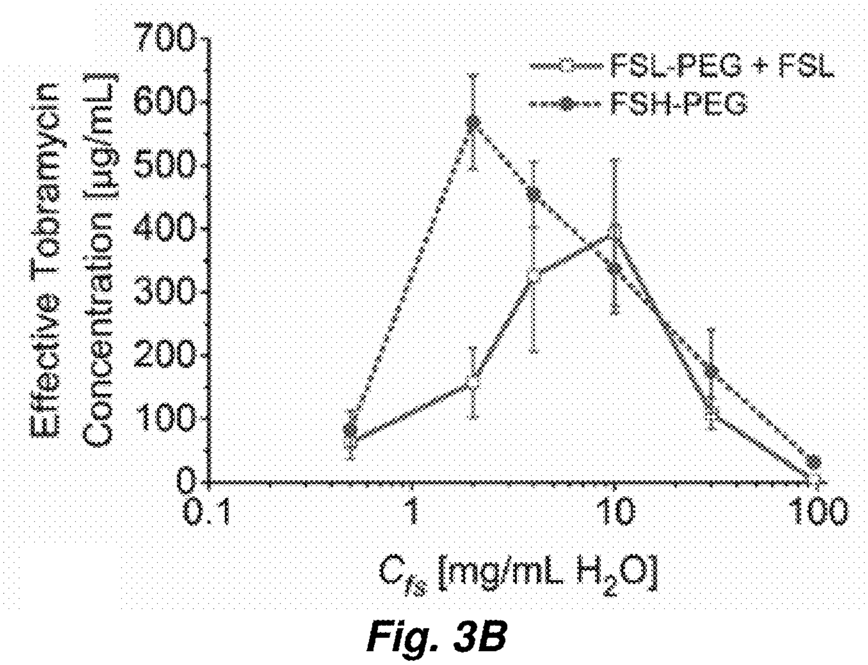
Figure 3C:
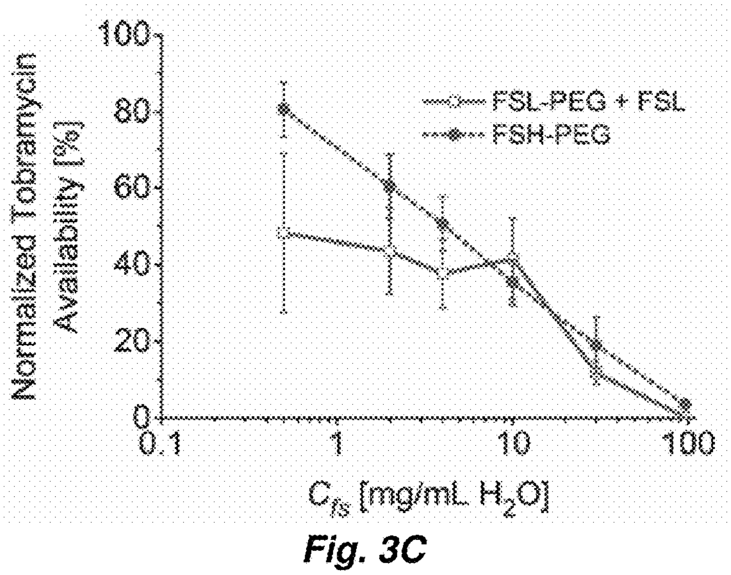

Emulsion tobramycin content, effective concentration, and normalized availability are shown in FIGS. 3A, 3B, and 3C, respectively, for emulsions ($V_{aq}$=2.5% and $C_{aq}$=40 mg/mL) using either FSH-PEG or FSL-PEG+FSL. Samples from negative control emulsions (i.e., without tobramycin) with 96 mg/mL $H_2O$ of either fluorosurfactant type produced no bacterial inhibition zones, thereby confirming that the inhibited bacterial growth observed was solely due to tobramycin content. Both fluorosurfactant type and concentration were observed to have significant ($p<0.01$) effects on tobramycin content (FIG. 3A). Tobramycin content was greater than 80% of the loaded drug mass at the larger $C_{fs}$ values examined for both fluorosurfactant types, thereby demonstrating sufficient drug emulsification within these ranges. However, content diminished as $C_{fs}$ decreased. For emulsions utilizing FSL-PEG+FSL, tobramycin content was shown to significantly decrease ($p<0.01$) at $C_{fs}\leq 2$ mg/mL $H_2O$. For FSH-PEG, tobramycin content was significantly decreased ($p<0.01$) only for the lowest $C_{fs}$ value examined (0.5 mg/mL $H_2O$). The diminished tobramycin content observed at the lower $C_{fs}$ values can be attributed to aqueous phase separation occurring prior to emulsion. Significant phase separation was seen at four-fold larger $C_{fs}$ values for FSL-PEG+FSL as compared to FSH-PEG, thereby demonstrating the superior ability of FSH-PEG to sufficiently emulsify the aqueous drug phase.

Effective tobramycin concentration (FIG. 3B) was smaller at both high and low $C_{fs}$, reaching a peak at intermediate values. Maximum effective concentrations were 393±115 μg/mL at $C_{fs}$=10 mg/mL $H_2O$ for FSL-PEG+FSL and 569±74 μg/mL at $C_{fs}$=2 mg/mL $H_2O$ for FSH-PEG. The normalized tobramycin availability calculated from the effective tobramycin concentration and content is shown in FIG. 3C. Tobramycin availability decreased substantially with increasing $C_{fs}$. Maximum availability was 48 and 81% for FSL-PEG+FSL and FSH-PEG, respectively, and occurred at the lowest $C_{fs}$ evaluated (0.5 mg/mL $H_2O$). Effects of fluorosurfactant type and concentration on effective tobramycin concentration (FIG. 3B) and normalized availability (FIG. 3C) were statistically significant ($p<0.01$).

Figure 4:
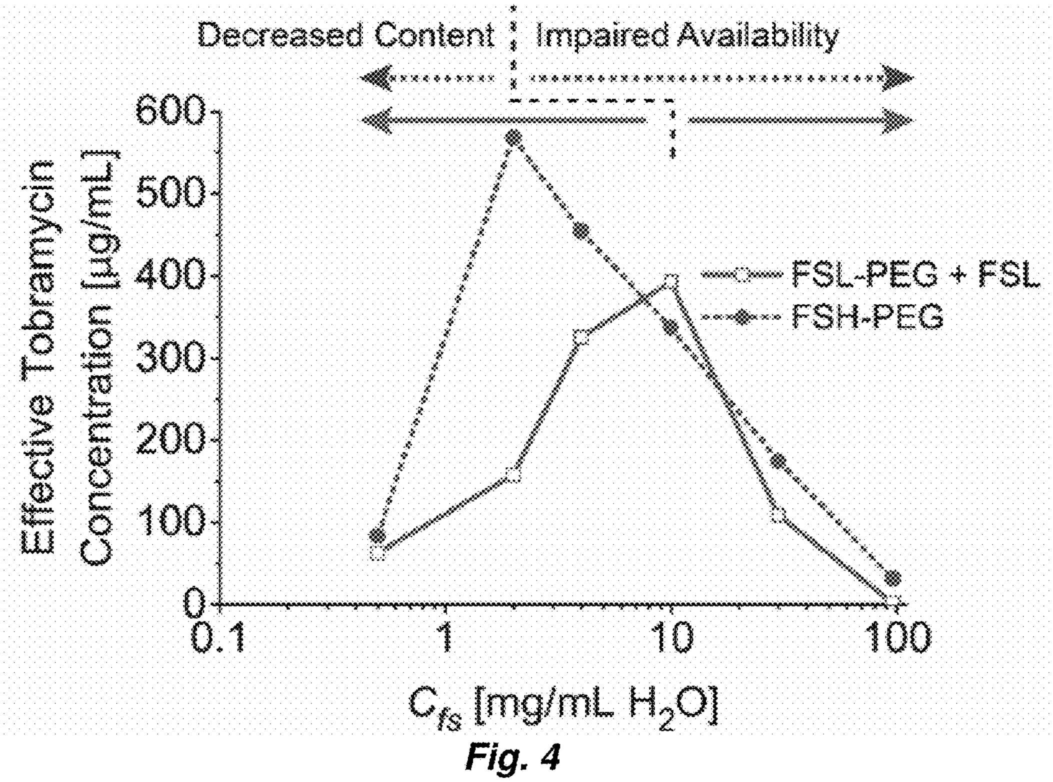
FIG. 4: Tobramycin availability as a function of $C_{fs}$ showing proposed causes of decreased effective tobramycin concentration observed over varying ranges of $C_{fs}$ for each fluorosurfactant type.

This data distinctly demonstrates two opposing effects of $C_{fs}$ on the effective tobramycin concentration encountered by a surface in contact with the emulsion. The decrease in effective concentration at $C_{fs}$ values below those of maximum effective concentration coincides with diminished tobramycin content due to inadequate emulsification. Thus, the measured decrease in effective tobramycin concentration at $C_{fs}$ values less than 10 and 2 mg/mL $H_2O$ for FSL-PEG+FSL and FSH-PEG, respectively, is predominantly due to a lack of drug rather than poor availability. However, as $C_{fs}$ was increased beyond these values, effective tobramycin concentration decreased while tobramycin content did not vary significantly and was reasonably close to the loaded mass. Thus, within a range of $C_{fs}$ values producing sufficient drug emulsification, increased $C_{fs}$ decreases the effective tobramycin concentration of the emulsion via reduced tobramycin availability. These effects are illustrated in FIG. 4.

Figure 5:
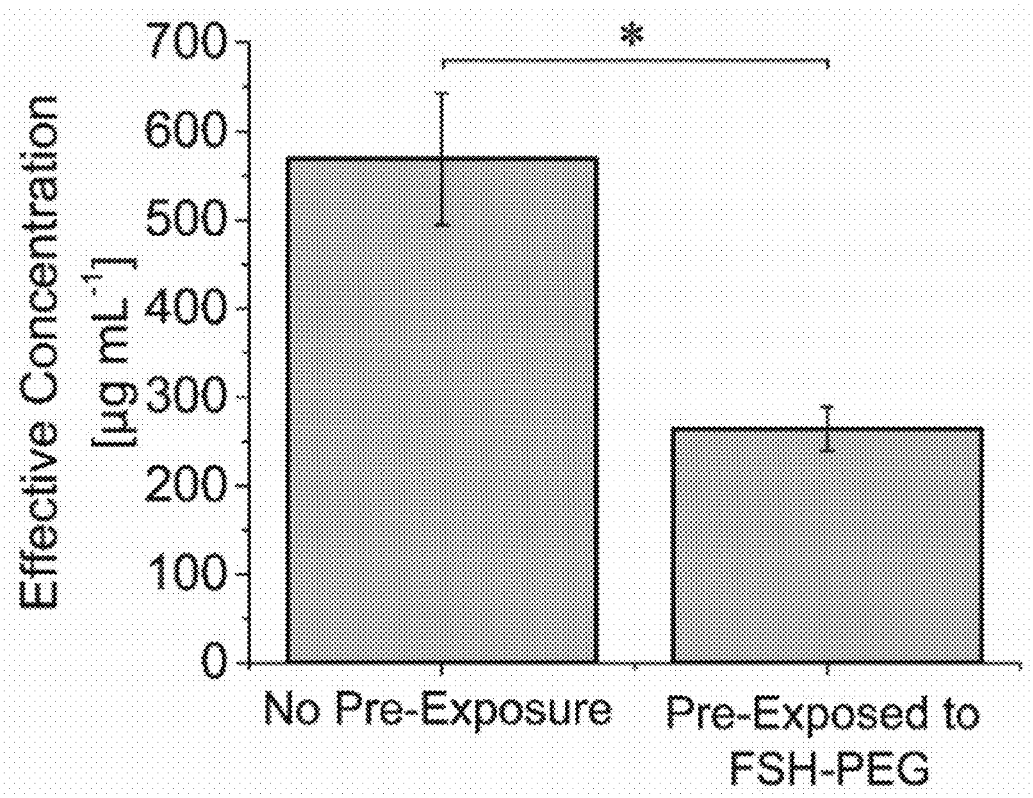
FIG. 5: Pre-exposure to FSH-PEG in PFC significantly decreases ($p<0.01$) effective tobramycin concentration for an emulsion formulation with maximum effective tobramycin concentration.

Pre-exposure of the agar well lumen to FSH-PEG in PFC significantly decreased ($p<0.01$) effective tobramycin concentration for the emulsion formulation with maximum effective tobramycin concentration ($C_{fs}$=2 mg/mL $H_2O$ of FSH-PEG, $V_{aq}$=2.5%, and $C_{aq}$=40 mg/mL; FIG. 5). Effective tobramycin concentrations for the trials with and without pre-exposure to FSH-PEG were 264±25 and 569±74 μg/mL, respectively. Thus, the brief exposure (10 minutes) of high concentrations of dissolved fluorosurfactant to the agar surface prior to emulsion loading reduced the effective concentration of emulsified tobramycin by greater than 50%. Such a result further confirms that fluorosurfactant undoubtedly reduces drug availability.

The intended effect of the fluorosurfactants is to assemble at the aqueous-PFC boundary of the drug-loaded droplets and delay their coalescence and creaming, thereby maintaining homogenous drug dispersion. Thus, it is reasonable to expect that increased levels of fluorosurfactant may also prevent droplet deposition on or coalescence with an aqueous surface in contact with the emulsion. However, even when left to completely evaporate within the agar well, drug availability has been shown to be significantly decreased. Thus, either a portion of the emulsion's drug content is ultimately unavailable to freely diffuse into the agar or the general diffusional capability of tobramycin is hindered. Due to the active, bactericidal nature of emulsified tobramycin following recovery via the described separation process, the formation of a chemical bond between tobramycin and fluorosurfactant molecules is an unlikely explanation for the observed lack of availability. Rather a more likely explanation is the impairment of mass transfer into an aqueous surface due to the fairly quick (effects shown after only 10 minutes of pre-exposure) aggregation of fluorosurfactant. Similar effects were also observed in vivo during APV pharmacokinetic trials evaluating tobramycin delivery via emulsion utilizing FSL-PEG+FSL at $C_{fs}$ values of 30 mg/mL $H_2O$ or greater (R. A. Orizondo, et al., *J Aerosol Med Pulm Drug Deliv*, DOI 10.1089/jamp.2015.1235(2016)). Those results showed low serum tobramycin concentrations and relatively large amounts of drug remaining in the lung, seemingly unavailable for systemic absorption, at a time that the PFC phase of the emulsion is expected to have largely evaporated. Thus, impaired drug diffusion into an agar surface at larger $C_{fs}$ explains this similar phenomenon occurring in the lung during APV.

Conclusions

The optimal emulsion formulation that will maximize the treatment efficacy of APV should maintain a spatially uniform distribution of drug while simultaneously maximizing drug availability to an aqueous surface such as mucus or a biofilm. The results of this work indicate that the effects of $C_{fs}$ on these two parameters may be working against each other to some degree. Thus, the optimal emulsion formulation must balance these opposing effects by utilizing the minimum concentration of fluorosurfactants necessary to maintain suitable drug dispersion for a short period necessary for drug preparation and delivery in order to also maximize drug availability. This is accomplished, for example, for FSL-PEG+FSL at a $C_{fs}$ value of 11 mg/mL $H_2O$ and at a lower value of 2 mg/mL $H_2O$ for FSH-PEG.

The following clauses illustrate various non-limiting aspects of the invention.

Clause 1: An emulsion comprising: a perfluorocarbon continuous phase; an aqueous dispersed phase comprising a therapeutic agent; and a block copolymer fluorosurfactant composition in an amount ranging from an amount effective to produce a stable emulsion of the aqueous phase in the perfluorocarbon and an amount above which the emulsion cannot deliver a therapeutically-effective amount of the therapeutic agent to a patient, wherein the block copolymer fluorosurfactant comprises a hydrophilic block and a perfluorocarbon block.

Clause 2: The emulsion of clause 1, wherein the amount of the fluorosurfactant composition is a minimal amount of fluorosurfactant effective to produce a stable emulsion of the aqueous phase in the perfluorocarbon, such as an amount that ranges from a minimum amount of the fluorosurfactant composition per unit volume of water in the emulsion effective to produce a stable emulsion to 20*log(1+the minimum amount of the fluorosurfactant composition per unit volume of water in the emulsion effective to produce a stable emulsion).

Clause 3: The emulsion of clause 1, wherein the hydrophilic block is a poly(oxy $C_{1-4}$alkylene), such as poly (oxyethylene), poly(oxypropylene), or poly(oxybutylene).

Clause 4: The emulsion of clause 3, wherein the hydrophilic block is a poly(oxyethylene), optionally having a Mw of from 100 Da to 5000 Da.

Clause 5: The emulsion of clause 1, wherein the fluorosurfactant is a triblock copolymer.

Clause 6: The emulsion of clause 5, wherein the triblock copolymer comprises two perfluorocarbon blocks and a single hydrophilic block.

Clause 7: The emulsion of any one of clauses 1-6, wherein the perfluorocarbon block of the fluorosurfactant is a perfluoroether.

Clause 8: The emulsion of clause 1, wherein the block copolymer has the structure:

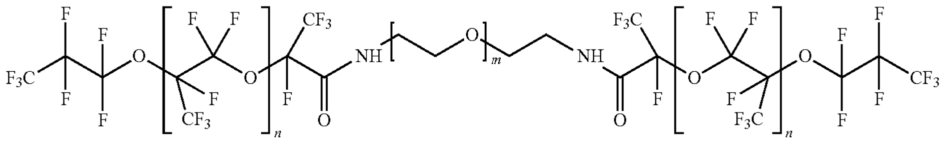

where m ranges from 10 to 100 and n ranges from 5 to 75, optionally m ranges from 22 to 75 and n ranges from 13 to 41.

Clause 9: The emulsion of any one of clauses 1-8, wherein the amount of fluorosurfactant is less than 11 mg/mL of water in the emulsion.

Clause 10: The emulsion of any one of clauses 1-9, wherein the perfluorocarbon is perfluorooctyl bromide, perfluorocycloether, perfluorooctane or a combination thereof.

Clause 11: The emulsion of any one of clauses 1-9, wherein the perfluorocarbon is perfluorooctyl bromide.

Clause 12: The emulsion of any one of clauses 1-9, wherein the perfluorocarbon is a mixture of perfluorocycloether and perfluorooctane.

Clause 13: The emulsion of any one of clauses 1-12, wherein the therapeutic agent comprises an antibiotic.

Clause 14: The emulsion of any one of clauses 1-12, wherein the therapeutic agent is an aminoglycoside antibiotic.

Clause 15: The emulsion of any one of clauses 1-12, wherein the therapeutic agent is tobramycin.

Clause 16: The emulsion of any one of clauses 1-15, wherein the emulsion comprises from 0.005 to 10% by volume (v/v) of the aqueous phase, such as from 0.01 to 5% by volume of the aqueous phase, and from 0.5 to 96 mg/ml of water of fluorosurfactant in the emulsion, such as from 0.5 to 11 mg/mL of water of fluorosurfactant in the emulsion.

Clause 17: The emulsion of clause 1, wherein the perfluorocarbon is perfluorooctyl bromide, perfluorocycloether, perfluorooctane or a combination thereof, the fluorosurfactant has the structure:

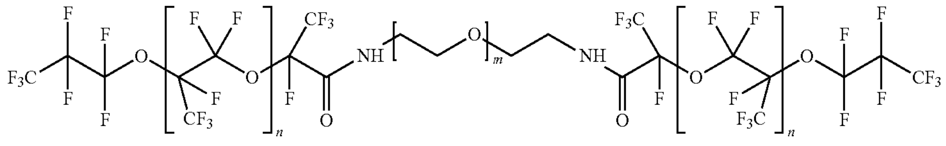

where m ranges from 10 to 100 and n ranges from 5 to 75, optionally m ranges from 22 to 75 and n ranges from 13 to 41, and the antibiotic is an aminoglycoside antibiotic, and optionally the antibiotic is tobramycin.

Clause 18: The emulsion of clause 17, wherein the emulsion comprises from 0.005 to 10% by volume of the aqueous phase, such as from 0.01 to 5% by volume of the aqueous phase, and from 0.5 to 96 mg/ml of water of fluorosurfactant in the emulsion, such as from 0.5 to 11 mg/mL of water of fluorosurfactant.

Clause 19: A kit comprising: in one or more vessels a perfluorocarbon; an aqueous solution comprising a therapeutically-effective amount of a therapeutic agent; and a block copolymer fluorosurfactant composition comprising a hydrophilic block and a perfluorocarbon block in an amount ranging from an amount effective to produce a stable emulsion of the aqueous phase in the perfluorocarbon and an amount above which the emulsion cannot deliver a therapeutically-effective amount of the therapeutic agent to a patient.

Clause 20: The kit of clause 19, wherein the amount of the fluorosurfactant composition is a minimal amount of fluorosurfactant effective to produce a stable emulsion of the aqueous phase in the perfluorocarbon, such as an amount that ranges from a minimum amount of the fluorosurfactant composition per unit volume of water in the emulsion effective to produce a stable emulsion to 20*log(1+the minimum amount of the fluorosurfactant composition per unit volume of water in the emulsion effective to produce a stable emulsion).

Clause 21: The kit of clause 19, wherein the hydrophilic block is a poly(oxy $C_{1-4}$alkylene), such as poly(oxyethylene), poly(oxypropylene), or poly(oxybutylene).

Clause 22: The kit of clause 21, wherein the hydrophilic block is a poly(oxyethylene), optionally having a Mw of from 100 Da to 5000 Da.

Clause 23: The kit of clause 19, wherein the fluorosurfactant is a triblock copolymer.

Clause 24: The kit of clause 23, wherein the triblock copolymer comprises two perfluorocarbon blocks and a single hydrophilic block.

Clause 25: The kit of any one of clauses 19-24, wherein the perfluorocarbon block of the fluorosurfactant is a perfluoroether.

Clause 26: The kit of clause 19, wherein the block copolymer has the structure:

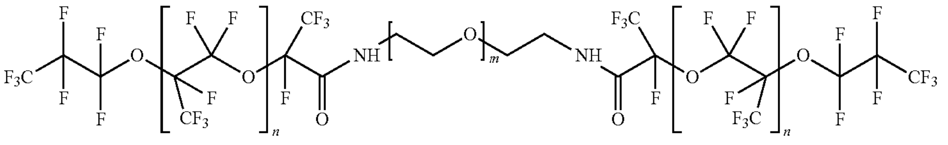

where m ranges from 10 to 100 and n ranges from 5 to 75, optionally m ranges from 22 to 75 and n ranges from 13 to 41.

Clause 27: The kit of any one of clauses 19-26, wherein the amount of fluorosurfactant is less than 11 mg/mL of water in the emulsion.

Clause 28: The kit of any one of clauses 19-27, wherein the perfluorocarbon is perfluorooctyl bromide, perfluorocycloether, perfluorooctane or a combination thereof.

Clause 29: The kit of any one of clauses 19-27, wherein the perfluorocarbon is perfluorooctyl bromide.

Clause 30: The kit of any one of clauses 19-27, wherein the perfluorocarbon is a mixture of perfluorocycloether and perfluorooctane.

Clause 31: The kit of any one of clauses 19-30, wherein the therapeutic agent comprises an antibiotic.

Clause 32: The kit of any one of clauses 19-30, wherein the therapeutic agent is an aminoglycoside antibiotic.

Clause 33: The kit of any one of clauses 19-30, wherein the therapeutic agent is tobramycin.

Clause 34: The kit of any one of clauses 19-33, wherein the emulsion comprises from 0.005 to 10% by volume of the aqueous phase, such as from 0.01 to 5% by volume of the aqueous phase, and from 0.5 to 96 mg/ml of water of fluorosurfactant in the emulsion, such as from 0.5 to 11 mg/mL of water of fluorosurfactant.

Clause 35: The kit of clause 19, wherein the perfluorocarbon is perfluorooctyl bromide, perfluorocycloether, perfluorooctane or a combination thereof, the fluorosurfactant has the structure:

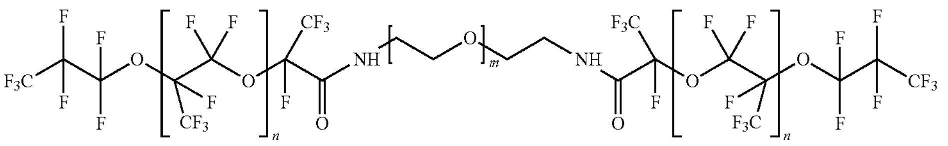

where m ranges from 10 to 100 and n ranges from 5 to 75, optionally m ranges from 22 to 75 and n ranges from 13 to 41, and the antibiotic is an aminoglycoside antibiotic, and optionally the antibiotic is tobramycin.

Clause 36: The kit of clause 35, wherein the emulsion comprises from 0.005 to 10% by volume of the aqueous phase, such as from 0.01 to 5% by volume of the aqueous phase, and from 0.5 to 96 mg/ml of water of fluorosurfactant in the emulsion, such as from 0.5 to 11 mg/mL of water of fluorosurfactant.

Clause 37: A method of delivering a therapeutic agent to lungs of a patient, comprising administering to the patient an emulsion according to any one of clauses 1-18.

Clause 38: The method of clause 37, wherein the emulsion is delivered as a spray, such as an aerosol.

Clause 39: The method of clause 37, wherein the emulsion is delivered by either partial liquid ventilation or total liquid ventilation.

Clause 40: A method of making emulsion comprising emulsifying: a perfluorocarbon; an aqueous solution comprising a therapeutic agent; and a block copolymer fluorosurfactant composition comprising a hydrophilic block and a perfluorocarbon block in an amount ranging from an amount effective to produce a stable emulsion of the aqueous phase in the perfluorocarbon and an amount above which the emulsion cannot deliver a therapeutically-effective amount of the therapeutic agent to a patient.

Clause 41: The method of clause 40, wherein the amount of the fluorosurfactant composition is a minimal amount of fluorosurfactant effective to produce a stable emulsion of the aqueous phase in the perfluorocarbon, such as an amount that ranges from a minimum amount of the fluorosurfactant composition per unit volume of water in the emulsion effective to produce a stable emulsion to 20*log(1+the minimum amount of the fluorosurfactant composition per unit volume of water in the emulsion effective to produce a stable emulsion).

Clause 42: The method of clause 40, wherein the hydrophilic block is a poly(oxy $C_{1-4}$alkylene), such as poly (oxyethylene), poly(oxypropylene), or poly(oxybutylene).

Clause 43: The method of clause 42, wherein the hydrophilic block is a poly(oxyethylene), optionally having a Mw of from 100 Da to 5000 Da.

Clause 44: The method of clause 40, wherein the fluorosurfactant is a triblock copolymer.

Clause 45: The method of clause 44, wherein the triblock copolymer comprises two perfluorocarbon blocks and a single hydrophilic block.

Clause 46: The method of any one of clauses 40-45, wherein the perfluorocarbon block of the fluorosurfactant is a perfluoroether.

Clause 47: The method of clause 40, wherein the block copolymer has the structure:

Clause 60: The method of clause 58, wherein the emulsion is delivered by either partial liquid ventilation or total liquid ventilation.

Clause 61: The method of any one of clauses 58-60, wherein the patient has cystic fibrosis.

Clause 62: The method of any one of clauses 58-61, wherein the active agent is tobramycin.

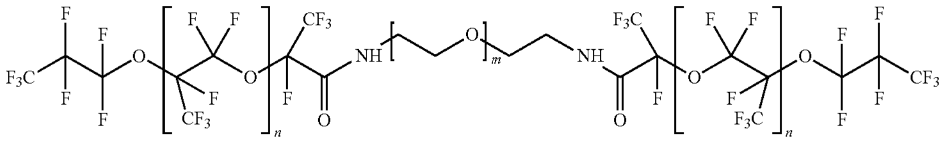

where m ranges from 22 to 75 and n ranges from 13 to 41.

Clause 48: The method of any one of clauses 40-47, wherein the amount of fluorosurfactant is less than 11 mg/mL of water in the emulsion.

Clause 49: The method of any one of clauses 40-48, wherein the perfluorocarbon is perfluorooctyl bromide, perfluorocycloether, perfluorooctane or a combination thereof.

Clause 50: The method of any one of clauses 40-48, wherein the perfluorocarbon is perfluorooctyl bromide.

Clause 51: The method of any one of clauses 40-48, wherein the perfluorocarbon is a mixture of perfluorocycloether and perfluorooctane.

Clause 52: The method of any one of clauses 40-51, wherein the therapeutic agent comprises an antibiotic.

Clause 53: The method of any one of clauses 40-52, wherein the therapeutic agent is an aminoglycoside antibiotic.

Clause 54: The method of any one of clauses 40-52, wherein the therapeutic agent is tobramycin.

Clause 55: The method of any one of clauses 40-54, wherein the emulsion comprises from 0.005 to 10% by volume of the aqueous phase, such as from 0.01 to 5% by volume of the aqueous phase, and from 0.5 to 96 mg/ml of water of fluorosurfactant in the emulsion, such as from 0.5 to 11 mg/mL of water of fluorosurfactant.

Clause 56: The method of clause 40, wherein the perfluorocarbon is perfluorooctyl bromide, perfluorocycloether, perfluorooctane or a combination thereof, the fluorosurfactant has the structure:

The present invention has been described in accordance with several examples, which are intended to be illustrative in all aspects rather than restrictive. Thus, the present invention is capable of many variations in detailed implementation, which may be derived from the description contained herein by a person of ordinary skill in the art.

We claim:

1. An emulsion comprising:

a perfluorocarbon continuous phase;

an aqueous dispersed phase comprising a therapeutic agent; and a fluorosufactant composition in an amount ranging from an amount effective to produce a stable emulsion of the aqueous phase in the perfluorocarbon and an amount above which the emulsion cannot deliver a therapeutically-effective amount of the therapeutic agent to a patient, wherein the fluorosurfactant composition comprises a block copolymer fluorosurfactant comprising a hydrophilic block and a perfluorocarbon block, wherein the amount of the fluorosurfactant composition, in mg/mL of water in the emulsion, ranges from a minimum amount of the fluorosurfactant composition effective to produce a stable emulsion to 20*log(1+the minimum amount of the fluorosurfactant composition effective to produce a stable emulsion).

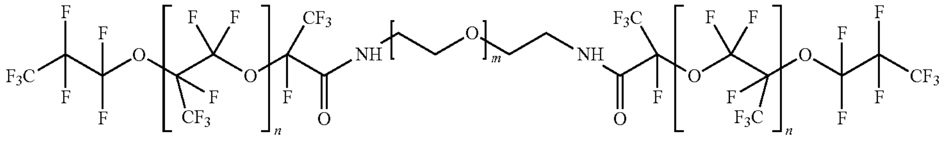

where m ranges from 10 to 100 and n ranges from 5 to 75, optionally m ranges from 22 to 75 and n ranges from 13 to 41, and the antibiotic is an aminoglycoside antibiotic, and optionally the antibiotic is tobramycin.

Clause 57: The method of clause 56, wherein the emulsion comprises from 0.005 to 10% by volume of the aqueous phase, such as from 0.01 to 5% by volume of the aqueous phase, and from 0.5 to 96 mg/ml of water of fluorosurfactant in the emulsion, such as from 0.5 to 11 mg/mL of water of fluorosurfactant.

Clause 58: A method of treating a lung infection in a patient, comprising administering to the lungs of a patient an emulsion according to any one of clauses 1-18.

Clause 59: The method of clause 58, wherein the emulsion is delivered as a spray, such as an aerosol.

2. The emulsion of claim 1, wherein the hydrophilic block is a poly(oxy$C_{1-4}$alkylene), such as poly(oxyethylene), poly(oxypropylene), or poly(oxybutylene).

3. The emulsion of claim 2, wherein the hydrophilic block is a poly(oxyethylene), optionally having a Mw of from 100 Da to 5000 Da.

4. The emulsion of claim 1, wherein the block copolymer fluorosurfactant is a triblock copolymer.

5. The emulsion of claim 4, wherein the triblock copolymer comprises two perfluorocarbon blocks and a single hydrophilic block.

6. The emulsion of claim 1, wherein the perfluorocarbon block of the fluorosurfactant is a perfluoroether.

7. The emulsion of claim 1, wherein the block copolymer fluorosurfactant has the structure:

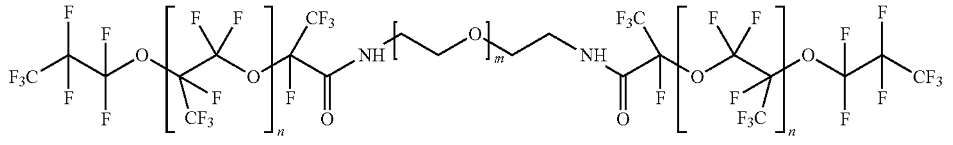

where m ranges from 22 to 75 and n ranges from 13 to 41.

8. The emulsion of claim 1, wherein the amount of fluorosurfactant is less than 11 mg/mL of water in the emulsion.

9. The emulsion of claim 1, wherein the perfluorocarbon is perfluorooctyl bromide, perfluorocycloether, perfluorooctane or a combination thereof.

10. The emulsion of claim 1, wherein the perfluorocarbon is perfluorooctyl bromide.

11. The emulsion of claim 1, wherein the perfluorocarbon is a mixture of perfluorocycloether and perfluorooctane.

12. The emulsion of claim 1, wherein the therapeutic agent comprises an antibiotic.

13. The emulsion of claim 1, wherein the therapeutic agent is tobramycin.

14. The emulsion of claim 1, wherein the emulsion comprises from 0.01 to 5% by volume of the aqueous phase, and wherein the amount of the fluorosurfactant composition is from 0.5 to 11 mg/mL of water in the emulsion.

15. A method of delivering a therapeutic agent to lungs of a patient, comprising administering to the patient an emulsion comprising:

a perfluorocarbon continuous phase;

an aqueous dispersed phase comprising a therapeutic agent; and a fluorosurfactant composition in an amount ranging from an amount effective to produce a stable emulsion of the aqueous phase in the perfluorocarbon and an amount above which the emulsion cannot deliver a therapeutically-effective amount of the therapeutic agent to a patient, wherein the fluorosurfactant composition comprises a block copolymer fluorosurfactant comprising a hydrophilic block and a perfluorocarbon block, wherein the amount of the fluorosurfactant composition, in mg/mL of water in the emulsion, ranges from a minimum amount of the fluorosurfactant composition effective to produce a stable emulsion to 20*log(1+the minimum amount of the fluorosurfactant composition effective to produce a stable emulsion).

16. The method of claim 15, wherein the emulsion is delivered as a spray, such as an aerosol.

17. The method of claim 15, wherein the emulsion is delivered by either partial liquid ventilation or total liquid ventilation.

18. A method of making emulsion comprising emulsifying: a perfluorocarbon; an aqueous solution comprising a therapeutic agent; and a fluorosurfactant composition comprising a block copolymer fluorosurfactant comprising a hydrophilic block and a perfluorocarbon block in an amount ranging from an amount effective to produce a stable emulsion of the aqueous phase in the perfluorocarbon and an amount above which the emulsion cannot deliver a therapeutically-effective amount of the therapeutic agent to a patient, wherein the amount of the fluorosurfactant composition, in mg/mL of water in the emulsion, ranges from a minimum amount of the fluorosurfactant composition effective to produce a stable emulsion to 20*log(1+the minimum amount of the fluorosurfactant composition effective to produce a stable emulsion).

19. The method of claim 18, wherein the block copolymer fluorosurfactant has the structure:

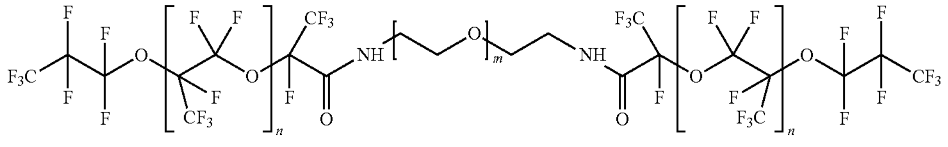

where m ranges from 22 to 75 and n ranges from 13 to 41.

* * * * *